United States Patent [19]

Horiuchi et al.

[11] Patent Number: 5,718,749
[45] Date of Patent: Feb. 17, 1998

[54] DENTAL GYPSUM BONDED INVESTMENT COMPOSITION

[75] Inventors: Haruhiko Horiuchi; Kenichi Iiyama; Koichi Mamada, all of Tokyo, Japan

[73] Assignee: GC Corporation, Tokyo, Japan

[21] Appl. No.: 748,789

[22] Filed: Nov. 14, 1996

[30] Foreign Application Priority Data

Nov. 17, 1995 [JP] Japan .................................. 7-322428
Sep. 18, 1996 [JP] Japan .................................. 8-266608

[51] Int. Cl.$^6$ ........................... B22C 1/08; C04B 11/00
[52] U.S. Cl. ..................... 106/38.35; 106/35; 106/778; 106/788
[58] Field of Search ....................... 106/35, 38.35, 106/778, 788; 523/116

[56] References Cited

U.S. PATENT DOCUMENTS

| | | | |
|---|---|---|---|
| 4,604,142 | 8/1986 | Kamohara et al. | 106/35 |
| 4,814,011 | 3/1989 | Kamohara et al. | 106/35 |
| 4,909,847 | 3/1990 | Ohi et al. | 106/35 |
| 5,304,239 | 4/1994 | Schwabe et al. | 106/35 |
| 5,373,891 | 12/1994 | Kato et al. | 106/35 |

FOREIGN PATENT DOCUMENTS

| | | | |
|---|---|---|---|
| 6-6336409 | 12/1994 | Japan . | |
| 7-164096 | 6/1995 | Japan . | |
| 2126571 | 3/1984 | United Kingdom | 106/35 |

OTHER PUBLICATIONS

WPIDS Abstract No. 84-218189, which is an abstract of Soviet Union Patent Specification No. 1,064,950 (Jan. 1984).
WPIDS Abstract No. 86-267743, which is an abstract Japanese Patent Specification No. 61-193741 (Aug. 1986).
Chemical Abstract No. 102-119689, which is an abstract Japanese Patent Specification No. 59-195561 (Nov. 1984).

*Primary Examiner*—Anthony Green
*Attorney, Agent, or Firm*—Oblon, Spivak, McClelland, Maier & Neustadt, P.C.

[57] ABSTRACT

A dental gypsum bonded investment composition comprising 100 parts by weight of a mixture comprising (a) α-hemihydrate gypsum as a binder and (b) quartz and/or cristobalite as a refractory material, and optionally, (c) one or more aggregates selected from the group consisting of metallic oxides, metallic carbides, and metallic nitrides, which can substitute a part of the refractory material, having from 0.01 to 1.0 part by weight of a poly-tetrafluoroethylene resin and optionally, from 0.001 to 0.05 part by weight of one or more anionic surfactants selected from the group consisting of alkylbenzenesulfonates and alkylsulfates mixed therewith, is disclosed. The dental gypsum bonded investment composition of the invention keeps the fine particles to have a stable performance without being removed by the pneumatic transportation at the time of production, has superior heat resistance, and can be used for casting of alloys having a high melting point such as casting alloys for metalceramic restorations.

8 Claims, No Drawings ural precision casting. More specifically, the invention provides a
DENTAL GYPSUM BONDED INVESTMENT COMPOSITION

FIELD OF THE INVENTION

The present invention relates to a dental gypsum bonded investment composition which is used for the dental precision casting. More specifically, the invention provides a dental gypsum bonded investment composition which is able to keep stable properties due to the trapping effect of poly-tetrafluoroethylene resin fine particles, while reducing losses of the fine particles at the time of pneumatic transportation in the investment production, and in which when a casting mold is heated at the time of the use of the investment, the poly-tetrafluoroethylene resin is gasified and reacted with gypsum (calcium sulfate) to form heat-resistant calcium fluoride ($CaF_2$), whereby a casting mold with high heat resistance can be prepared.

BACKGROUND OF THE INVENTION

Dental metal restorations are prepared by the procedures in which the shape of a restoration is formed using a wax material by means of the precision casting technology in the lost wax process, a sprue former (a sprue for molten metal) is provided thereon, the resulting material is invested with a dental investment, after the dental investment has set, the sprue former is pulled away, the wax is burnt out, and a thus formed void is then poured with a molten metal. In particular, since the dental metal restoration is set in the oral cavity and used for the purpose of restoring a defective tooth, it is required to have a high dimensional precision. For this reason, in order to obtain a dental metal restoration with superior precision, it is necessary to compensate the casting shrinkage of the metal by utilizing the expansion of the dental investment at the time of setting and of heating.

As the dental investment, there are two kinds, i.e., a gypsum bonded investment comprising a refractory material, such as quartz and/or cristobalite, having α-hemihydrate gypsum as a binder mixed therewith, and a phosphate bonded investment with high heat resistance, which comprises a refractory material, such as quartz and/or cristobalite, having ammonium dihydrogen phosphate and magnesium oxide as binders mixed therewith. In case of precious metal-based dental casting alloys for inlays, crowns, and bridges that the JIS standards prescribe to have a liquidus point not higher than 1,000°–1,100° C. [dental casting silver alloys (JIS T 6108), dental casting gold-silver-palladium alloys (JIS T 6106), and dental casting gold alloys (JIS T 6116)], the gypsum bonded investment is used, while in case of dental precious metal casting alloys for metal-ceramic restorations having a so high liquidus point (1,100° C. or higher) that they are resistant to the seizing works of the porcelain (about 1,000° C.) after the casting, the phosphate bonded investment is used.

In case that the gypsum bonded investment is compared with the phosphate bonded investment, the former is superior to the latter with respect to the operabilities in, e.g., the mixing works of an investment powder with liquids (such as water and exclusive colloidal silica solutions) and the casting works at the time of investment. On the other hand, the latter is superior to the former with respect to the heat resistance. Also, since the gypsum bonded investment comprises gypsum and silica (quartz and/or cristobalite) as major components, while the phosphate investment is composed of ammonium dihydrogen phosphate, magnesium oxide, and silica, the former is cheaper than the latter from the cost standpoint. In addition, in the gypsum bonded investment, the mixing liquid is water, while in the phosphate bonded investment, in order to obtain a predetermined expansion value, the exclusive solution (colloidal silica solution) or the like is required. Accordingly, though the gypsum bonded investment is much advantageous from the standpoints of operabilities and costs, it is not always satisfactory with respect to the heat resistance as a casting alloy for metal-ceramic restorations. Thus, it likely causes casting defects such as casting cavities and surface chapping on the casting surface, and hence, such is presently a neck technique for the gypsum bonded investment.

Further, in order to obtain metal restorations that are required to have a high dimensional precision, in dental investments, it is required that the expansion at the time of setting (setting expansion value) and the expansion at the time of heating (thermal expansion value) are strictly controlled so that they are adjusted so as to make it always possible to stably compensate the casting shrinkage. As factors which influence the setting expansion value and thermal expansion value, the particle size distribution of the investment particles is an important factor. When the particle size distribution changes, the setting expansion value and thermal expansion value vary, whereby the ability to compensate the casting shrinkage is changed, and influences against the dimensional precision of the metal restoration ultimately appear. For this reason, to control the particle size distribution of the dental investment is an important control item in the production of dental investments.

The outline of the production step of dental gypsum bonded investments is as follows:

(1) A grinding step of a refractory material (e.g., quartz, cristobalite, etc.);

(2) A step for adding the ground refractory material with α-hemihydrate gypsum as a binder and further grinding and mixing the mixture;

(3) An adjustment step of the setting time after the grinding and mixing, the fluidity, the particle size, and so on; and (4) A wrapping step.

Usually, the steps (1) and (2) are carried out in a batch processing apparatus such as a ball mill, and the adjustment step (3) is carried out prior to the discharge from the mill. After the adjustment, the powder discharged from the mill is transferred into the wrapping step (4). In general, in order to transport the dental gypsum bonded investment to the wrapping step, a pneumatic transportation apparatus utilizing an air is used.

The pneumatic transportation apparatus as referred to herein is an apparatus for mixing the powder with an air flow and transporting the mixture, and its system includes a force feed system and a suction system. In any of these systems, it is necessary to ultimately separate the powder from the air flow, and a cyclone separator is generally used for achieving the separation. However, in the cyclone separator, a phenomenon in which the fine powder particles go with the air flow without being separated from the air flow, are trapped by an air bag filter set in an air exhaust port of the cyclone separator and then disposed, or the finer particles pass through the air bag filter and are released into the air, occurs. Thus, a phenomenon in which the particle size distribution of the dental gypsum bonded investment at the time of the discharge from the mill is different from that after the pneumatic transportation occurs. As a result, an inconvenient phenomenon in which after the pneumatic transportation, the fine particles in the dental gypsum bonded investment are reduced as compared with those before the transportation, so that various properties such as the setting expansion value and the thermal expansion value change, whereby the performance to be expected as the dental gypsum bonded investment can not exhibit, occurs.

SUMMARY OF THE INVENTION

The present invention is aimed to develop a dental gypsum bonded investment composition which overcomes the above described various problems of the conventional techniques, is imparted with high heat resistance in addition to inherent superior properties in the operabilities, costs, etc. owned by gypsum bonded investments, and even upon casting with a casting alloy for metal-ceramic restorations, causes neither casting cavities nor surface chapping on the casting, and in which during the pneumatic transportation at the time of the production of investments, fine powders are surely trapped and ultimately remain in the investment product, and the expected performance is stably obtained, whereby metal restorations with high dimensional precision are always obtained.

In order to achieve the above-described aim, the present inventors made extensive and intensive investigations. As a result, it has been found that if a powdery composition composed of α-hemihydrate gypsum as a binder and quartz and/or cristobalite as a refractory material is mixed with a predetermined amount of a poly-tetrafluoroethylene resin, not only at the time of the production, due to the trapping effect of fine particles of the poly-tetrafluoroethylene resin, fine particles in the powdery composition are surely separated from an air flow by a cyclone separator set in the final stage of the pneumatic transportation, whereby a dental gypsum bonded investment keeping always stable properties can be obtained, but also at the time of the use, upon heating a casting mold, the poly-tetrafluoroethylene resin is gasified and reacted with gypsum (calcium sulfate) to form heat-resistant calcium fluoride ($CaF_2$), whereby a casting mold with high heat resistance can be prepared. Also, it has been found that if this dental gypsum bonded investment composition is mixed with one or more anionic surfactants selected from the group consisting of alkylbenzenesulfonates and alkylsulfates, the mixing operabilities are improved and that if a part of the refractory material is replaced by and mixed with one or more aggregates selected from the group consisting of metallic oxides, metallic carbides, and metallic nitrides, the surface chapping of the casting and the seizing of the investment can be inhibited.

Thus, a first object of the present invention is to provide a dental gypsum bonded investment composition comprising 100 parts by weight of a mixture comprising (a) α-hemihydrate gypsum as a binder and (b) quartz and/or cristobalite as a refractory material, having from 0.01 to 1.0 part by weight of a poly-tetrafluoroethylene resin mixed therewith.

A second object of the present invention is to provide a dental gypsum bonded investment composition comprising 100 parts by weight of a mixture comprising (a) α-hemihydrate gypsum as a binder and (b) quartz and/or cristobalite as a refractory material, having from 0.01 to 1.0 part by weight of a poly-tetrafluoroethylene resin and from 0.001 to 0.05 part by weight of one or more anionic surfactants selected from the group consisting of alkylbenzenesulfonates and alkylsulfates mixed therewith.

A third object of the present invention is to provide a dental gypsum bonded investment composition comprising 100 parts by weight of a mixture comprising (a) α-hemihydrate gypsum as a binder, (b) quartz and/or cristobalite as a refractory material, and (c) one or more aggregates selected from the group consisting of metallic oxides, metallic carbides, and metallic nitrides, having from 0.01 to 1.0 part by weight of a poly-tetrafluoroethylene resin mixed therewith.

A fourth object of the present invention is to provide a dental gypsum bonded investment composition comprising 100 parts by weight of a mixture comprising (a) α-hemihydrate gypsum as a binder, (b) quartz and/or cristobalite as a refractory material, and (c) one or more aggregates selected from the group consisting of metallic oxides, metallic carbides, and metallic nitrides, having from 0.01 to 1.0 part by weight of a poly-tetrafluoroethylene resin and from 0.001 to 0.05 part by weight of one or more anionic surfactants selected from the group consisting of alkylbenzenesulfonates and alkylsulfates mixed therewith.

DETAILED DESCRIPTION OF THE INVENTION

In the dental gypsum bonded investment composition according to the present invention, in 100 parts by weight of the mixture comprising (a) α-hemihydrate gypsum as a binder, (b) quartz and/or cristobalite as a refractory material, and (c) one or more aggregates which may be further added, selected from the group consisting of metallic oxides, metallic carbides, and metallic nitrides, the amount of the binder (a) is preferably in the range of from 20 to 40 parts by weight, and consequently, the amount of the refractory material (b) is in the range of from 60 to 80 parts by weight. In case that the aggregate (c) is added, it is suitable that a part of the refractory material (b) is replaced by the aggregate (c). In this case, it is preferred that the amount of the aggregate (c) is in the range of from 2 to 40 parts by weight, while the amount of the refractory material (b) is in the range of from 20 to 78 parts by weight.

When tetrafluoroethylene is polymerized in an aqueous solution, a finely particulate resin of poly-tetrafluoroethylene having a mean particle size of from about 0.05 to 5 μm is obtained. Since the molecular chains of this fine resin are low in the intermolecular cohesive force, and upon application with even a slight compressive or shearing stress, the resin becomes in a fine spider-web fibrous state, the poly-tetrafluoroethylene resin in the spider-web fibrous state traps fine particles in the gypsum bonded investment. Accordingly, in case that the investment particles are subjected to pneumatic transportation, it is prevented that only the fine particles are trapped by an air bag filter set in an air exhaust port of a cyclone separator without being separated from an air flow by the cyclone separator and that the fine particles pass through the air bag filter and are released into the air.

Specifically, in the production of the dental gypsum bonded investment, the fine poly-tetrafluoroethylene resin is added in a mill in the grinding step of the refractory material and the binder, and a shearing or compressive stress by the mill is also applied to the poly-tetrafluoroethylene resin. Since in the poly-tetrafluoroethylene resin, the C—C bonds in the main chains of the molecular chains are strong, while the intermolecular attraction force against other molecular chains is extremely low, the poly-tetrafluoroethylene molecule having a shearing or compressive force applied thereto becomes in a finely fibrous state. This fiber is present in a state such that it clings to the fine particles of the refractory material, the binder, and the like in the gypsum bonded investment and is uniformly distributed in the investment powder, to thereby trap the fine particles. This phenomenon is already confirmed through the observation by a scanning-type electron microscope, and a phenomenon in which the investment particles cohere in the appearance occurs. However, since this phenomenon is different from minute cohesion of the fine particles which occurs by the operation of granulating usual particles but is of light cohesion of the powder in a state that the fine particles are trapped in the mesh of the fine fiber, no phenomenon which influences the characteristics as the dental gypsum bonded investment occurs.

Since the fine particles in the gypsum bonded investment trapped in the poly-tetrafluoroethylene resin fine fiber continue to keep the cohesive state to the tetrafluoroethylene resin during the pneumatic transportation and are surely separated from an air flow by a cyclone separator set in the final stage of the pneumatic transportation, it is prevented that only the fine particles are trapped by an air bag filter set in an air exhaust port of the cyclone separator and that the fine particles pass through the air bag filter and are released into the air. Thus, since the fine particles in the gypsum bonded investment are not removed, phenomena in which the characteristic values of the gypsum bonded investment, in particular, the setting expansion value and the thermal expansion value, are lowered after the pneumatic transportation as seen in gypsum bonded investments having no poly-tetrafluoroethylene resin added thereto, or the compressive strength is lowered after the setting, can be prevented.

Also, the dental gypsum bonded investment composition according to the present invention is mixed with water and used for making a casting mold, and after setting, is charged into a furnace. In the step for heating the casting mold in the furnace, the fibrous poly-tetrafluoroethylene resin is changed to a hydrogen fluoride gas. The hydrogen fluoride gas with high activity is immediately reacted with anhydrous gypsum ($CaSO_4$) to which α-hemihydrate gypsum ($CaSO_4 \cdot \frac{1}{2}H_2O$) present as the binder in the casting mold has been changed upon heating at high temperatures, to form calcium fluoride ($CaF_2$, melting point: 1,418° C., boiling point: 2,500° C.) with high heat resistance. Since this reaction takes place from the particle surfaces, and the formed calcium fluoride is finely and uniformly distributed in the casting mold, to thereby prevent the gypsum with poor heat resistance from direct contact with the molten alloy and improve the heat resistance as the casting mold, even when the casting mold is casted with a casting alloy for metal-ceramic restorations, the reaction between the molten alloy and the casting mold can be reduced as far as possible.

As a result, the following defects are dissolved.

(1) Seizing of the casting mold onto the casting surfaces;

(2) Formation of casting cavities distributed in the interior of the casting by the gas formed through the decomposition reaction of gypsum; and (3) Surface chapping of the casting by the gas formed through the decomposition reaction of gypsum.

Thus, it is possible to undergo casting of casting alloys for metal-ceramic restorations with a gypsum bonded investment.

If the addition amount of the poly-tetrafluoroethylene resin to be mixed is less than 0.01 part by weight, the improvement in the heat resistance as the casting mold is unsatisfactory so that it is difficult to completely prevent the casting defects of the casting alloys for metal-ceramic restorations. Also, at the time of the production, the action of the gypsum bonded investment to trap the fine particles is unsatisfactory so that the effect for preventing the losses of the fine particles by the pneumatic transportation does not sufficiently exhibit, whereby the setting expansion value and the thermal expansion value, both of which are important properties for the gypsum bonded investment, become unstable. For these reasons, the lower limit of the addition amount of the poly-tetrafluoroethylene resin was determined to be 0.01 part by weight.

On the other hand, the reasons why the upper limit of the addition amount of the poly-tetrafluoroethylene resin was determined to be 1.0 part by weight are as follows.

As described previously, when the poly-tetrafluoroethylene resin is applied with a shearing or compressive stress, it becomes in the finely fibrous state. If the addition amount of the poly-tetrafluoroethylene resin is in excess, the resin not only exhibits an action to trap the fine particles, but also acts for the large particles, whereby a phenomenon in which the powder causes the cohesion in a granular state occurs. As a result, the same tendency as in the case that the particle size distribution changes is found, and an inconvenience is generated such that the various properties such as the setting expansion value and the thermal expansion value change, whereby the performance expected as the dental gypsum bonded investment does not exhibit.

Also, upon the microscopic observation of the microsystem of the dental gypsum bonded investment after setting and heating, the particles of silica and the like usually cling to the gypsum crystallized in a needle-like state. If the tetrafluoroethylene resin is excessively added, calcium fluoride is excessively formed so that the spaces of the gypsum crystal are clogged, whereby the breathability of the casting mold becomes worse, leading to occurrence of casting defects (formation of casting cavities just under the sprue, back pressure porosity, formation of hot spots, etc.) caused by the shortage of the breathability. In addition, since the formation of calcium fluoride increases the strength of the casting mold after heating as far as possible, the formation of excessive calcium fluoride requires much labors at the time of excavation of the casting after casting, whereby the operabilities are remarkably impaired. For these reasons, the upper limit of the addition amount of the poly-tetrafluoroethylene resin was determined to be 1.0 part by weight.

Next, with respect to the case that one or more anionic surfactants selected from the group consisting of alkylbenzenesulfonates and alkylsulfates are added in an amount of from 0.001 to 0.05 part by weight, the reasons are described hereinafter.

The poly-tetrafluoroethylene resin is very high in water repellency, and in case that a gypsum bonded investment containing the same is mixed with water, the operation feel in use called "affinity with water" is adversely affected. Specifically, the wettability between the powder and water becomes worse, and the powder can not be mixed with water within a short period of time but becomes in a state that the powder floats over the water, whereby the mixing operation is hardly effected. While such properties do not directly influence the performance and properties of the gypsum bonded investment itself, they raise problems in the operation at the time of use including the mixing properties. In order to overcome these problems, if an anionic surfactant is added to improve the wettability between the powder and water, the mixing properties can be improved.

Examples of alkylbenzenesulfonates which can be used as the anionic surfactant include sodium dodecylbenzenesulfonate; and examples of alkylsulfates which can also be used as the anionic surfactant include sodium laurylsulfate, potassium laurylsulfate, sodium myristylsulfate, sodium cetylsulfate, and sodium stearylsulfate.

With respect to the addition amount of the anionic surfactant, since it is already confirmed that if the addition amount is 0.001 part by weight or more, the "affinity with water" is improved, the lower limit of the addition amount was determined to be 0.001 part by weight. On the other hand, the reasons why the upper limit of the addition amount was determined to be 0.05 part by weight are as follows. That is, this is because although the "affinity with water" at the time of mixing is improved as the addition amount increases, it was confirmed that if the addition amount exceeds a certain level, "setting time", "preservability", and "compressive strength", all of which are important characteristics for the investment, are adversely affected. In particular, the lowering in the "compressive strength" causes casting defects such as casting flash at the time of casting. Since it is already proven by experiments that the addition amount in which the characteristics of the gypsum bonded investment are not adversely affected in practical use is 0.05 part by weight, the addition amount of the anionic surfactant was determined to be 0.05 part by weight.

Next, the reasons why one or more aggregates selected from the group consisting of metallic oxides, metallic carbides, and metallic nitrides are added are described hereinafter.

By the addition of the poly-tetrafluoroethylene resin, among the casting defects caused by the shortage of the heat resistance, the surface chapping of the casting and the formation of casting cavities are found to be thoroughly improved. However, in case that the addition amount of the poly-tetrafluoroethylene resin is small as from 0.01 to 0.1 part by weight, there is a case that the effect for preventing the seizing of the gypsum bonded investment on the surface of the casting is insufficient. As a coutermeasure against this problem, it can be considered to add metallic oxides, metallic carbides, metallic nitrides, or the like as an aggregate to the gypsum bonded investment. Specifically, examples of metallic oxides include oxides of aluminum, yttrium, zirconium, chromium, titanium, and magnesium; examples of metallic carbides include carbides of tungsten, niobium, tantalum, silicon, zirconium, boron, molybdenum, chromium, and titanium; and examples of metallic nitrides include nitrides of aluminum, chromium, silicon, boron, and titanium.

In case that metallic oxides, metallic carbides, or metallic nitrides are added as the aggregate to the gypsum bonded investment for replacing a part of the refractory material, the aggregate is preferably added in an amount of from 2 to 40 parts by weight. In case that the addition amount of the aggregate is less than 2 parts by weight, satisfactory improvements in the effect for preventing the seizing of the investment caused by the addition of the aggregate are not found. The metallic oxide, metallic carbide, or metallic nitride as the aggregate generates only the expansion based on the thermal expansion coefficient inherent to each of the substances even at the time of heating, but does not generate a large expansion based on the transformation of the crystal structure caused by heating as seen in quartz and cristobalite. Accordingly, when an excess of the aggregate is mixed, though the heat resistance is improved, the amount of thermal expansion of the gypsum bonded investment itself is lowered, and hence, the compensation of the casting shrinkage of the alloy is insufficient so that the adaptation of the casting becomes worse. As a result of investigations of the Examples and Comparative Examples, it was found that in order to obtain castings which can be put into clinical use, the sum of the setting expansion value and the thermal expansion value of the gypsum bonded investment is required to be 1.5% or higher. Also, in order to keep a predetermined amount of thermal expansion while depressing the lowering in the amount of thermal expansion, even in case that the aggregate is added, its amount is desirably not more than 40 parts by weight.

The present invention is hereunder described in more detail with reference to the following Examples and Comparative Examples.

EXAMPLES

In each of the Examples, the compounding was carried out in the composition shown in Table 1, and in each of the Comparative Examples, the compounding was carried out in the composition shown in Table 4. Then, various tests as described below were carried out, and the comparison between the Examples and the Comparative Examples was made. The test results are summarized and shown in Tables 2 and 3 as well as in Tables 5 and 6.

[Preparation of Samples]

Grinding and mixing were carried out on a scale that the total weight of an investment is 50 kg using a ball mill for test compounding having an internal volume of 100 liters.

First of all, quartz and/or cristobalite as a refractory material and a poly-tetrafluoroethylene resin powder were charged in the ball mill, and the mixture was ground until the refractory material had exhibited a predetermined particle size distribution. Thereafter, α-hemihydrate gypsum as a binder and if the case may be, metallic oxides, metallic carbides, or metallic nitrides and anionic surfactants were further charged in the ball mill, followed by grinding and mixing. After adjusting the setting time as well as the fluidity, the mixture was discharged from the ball mill and then stored in a hopper.

The poly-tetrafluoroethylene resin powder was present in such a state that it was applied with a shearing or compressive stress in the grinding and mixing step of the refractory material and the binder, to exhibit a finely fibrous form, whereby it trapped the fine particles of the refractory material and of the binder. From the gypsum bonded investment stored in the hopper, specimens each having a weight of 1 kg were randomly sampled five times for testing the characteristics to collect samples of 5 kg in total. On the other hand, the remaining gypsum bonded investment of 45 kg was subjected to pneumatic transportation by means of a pneumatic transportation apparatus, and the inspection was made to what degree the fine particles of the gypsum bonded investment were lost by the pneumatic transportation and how the respective characteristics of the gypsum bonded investment were influenced thereby. After the pneumatic transportation, specimens each having a weight of 1 kg were randomly sampled to collect samples of 5 kg in total in the same manner as in the case before the pneumatic transportation.

[Testing Methods of Characteristics]

Each sample was measured with respect to characteristics of a gypsum bonded investment before and after the pneumatic transportation according to the procedures defined in JIS T 6601 "Gypsum Bonded Investments For Dental Casting". Also, the degree of losses of the fine particles was evaluated in such a manner that the particle size distribution was automatically measured in the measurement range B by means of a particle size distribution analyzer "Model SALD1100" manufactured by Shimadzu Corporation and that the volume percentage of the particles having a size not greater than 1.9 μm was compared.

The fitness precision of the casting was carried out in the following manner. That is, a wax pattern was prepared in a customary manner by using a crown model of an A.D.A. No. 2 specimen manufactured by Nisshin Dental Products Incorporated and invested by each of the gypsum bonded investments. Sixty minutes after the initiation of mixing, heating was started, the temperature was elevated to 700° C. over 150 minutes, and the casting mold was moored for 30 minutes, whereby it was made uniform at 700° C. Thereafter, the casting mold was casted with a dental casting gold alloy for metal-ceramic restorations [a trade name: G-Cera Bond Type I Gold, manufactured by GC Corporation] by using a dental centrifugal casting machine, and after excavation, the casting was washed with running water by using a nylon brush. After removing the investment seized on the casting by a sandblast treatment with glass beads having a particle size of 150 μm at a pressure of 0.2 MPa, the casting was returned to the crown model, the degree of lifting from the model was measured by means of a projector, and the fitness precision was evaluated according to the size.

Each of the characteristic values was a mean value of five times measured repeatedly with respect to the samples each having a weight of 1 kg before and after the pneumatic transportation, and the degree of scattering was expressed in terms of standard deviation.

Also, the casting defects were evaluated in the following manner. That is, casting molds were prepared in the same procedures as in those for evaluation of the fitness precision as described above by using a Natural Wax Pattern-C which is a ready-made wax pattern manufactured by Nisshin Dental Products Incorporated and casted with a dental casting gold alloy for metal-ceramic restorations [a trade name: G-Cera Bond Type I Gold, manufactured by GC Corporation, liquidus point: 1,200° C.] and a dental casting palladium alloy for metal-ceramic restorations [a trade name: G-Cera Bond Type III Palladium, manufactured by GC Corporation, liquidus point: 1,290° C.], respectively by means of a dental centrifugal casting machine. After allowing each casting mold to stand for cooling to the room temperature, the casting was excavated according to the customary manner and washed by using a nylon brush, and the seizing state of the investment, the surface chapping of the casting, and the formation of casting cavities were visually evaluated.

TABLE 1

[Compositions of Examples 1 to 12]

| | | Composition (part by weight) | | | |
|---|---|---|---|---|---|
| | Binder | Refractory Material | Aggregate | Poly-tetra-fluoro ethylene Resin | Anionic Surfactant |
| Example 1 | α-Hemi-hydrated Gypsum 27 | Quartz 45/ Cristo-balite 28 | — | 0.01 | — |
| Example 2 | α-Hemi-hydrated Gypsum 30 | Cristo-balite 70 | — | 0.1 | — |
| Example 3 | α-Hemi-hydrated Gypsum 33 | Quartz 67 | — | 1.0 | — |
| Example 4 | α-Hemi-hydrated Gypsum 27 | Quartz 45/ Cristo-balite 28 | — | 0.3 | Sodium Lauryl-sulfate 0.001 |
| Example 5 | α-Hemi-hydrated Gypsum 30 | Cristo-balite 70 | — | 0.5 | Sodium Myristyl-sulfate 0.002/ Sodium Cetyl-sulfate 0.002 |
| Example 6 | α-Hemi-hydrated Gypsum 33 | Quartz 67 | — | 1.0 | Sodium Dodecyl-benzene-sulfonate 0.01 |
| Example 7 | α-Hemi-hydrated Gypsum 27 | Quartz 44/ Cristo-balite 27 | Silicon Carbide 1/ Boron Nitride 1 | 0.01 | — |
| Example 8 | α-Hemi-hydrated Gypsum 27 | Quartz 43/ Cristo-balite 26 | Titanium Oxide 2/ Titanium Carbide 2 | 0.01 | — |
| Example 9 | α-Hemi-hydrated Gypsum 33 | Quartz 61 | Aluminum Oxide 3/ Titanium Oxide 3 | 0.2 | — |
| Example 10 | α-Hemi-hydrated Gypsum 27 | Quartz 40/ Cristo-balite 23 | Niobium Carbide 5/ Zirconium Oxide 5 | 0.5 | Sodium Stearyl-sulfate 0.03 |
| Example 11 | α-Hemi-hydrated Gypsum 30 | Cristo-balite 50 | Titanium Nitride 10/ Silicon Carbide 10 | 1.0 | Isopropyl Palmitate 0.02/ Sodium Cetyl-sulfate 0.02 |
| Example 12 | α-Hemi-hydrated Gypsum 30 | Cristo-balite 30 | Titanium Carbide 20/ Zirconium Oxide 20 | 1.0 | Sodium Lauryl-sulfate 0.01/ Sodium Stearyl sulfate 0.01 |

TABLE 2

[Various Characteristics (A) of Examples 1 to 12]

| | Setting Expansion Value (%) | Thermal Expansion Value (%) | Compressive Strength (MPa) | Volume of Particles Not Greater Than 1.9 μm (%) | Fitness Precision (Amount of Lifting) (mm) |
|---|---|---|---|---|---|
| Before the Pneumatic Transportation | | | | | |
| Example 1 | 0.90 (0.04) | 1.35 (0.02) | 4.4 (0.2) | 12.7 (0.3) | 0.01 (0.01) |
| Example 2 | 0.50 (0.02) | 1.44 (0.02) | 5.0 (0.2) | 11.4 (0.3) | 0.01 (0.01) |
| Example 3 | 0.73 (0.03) | 0.81 (0.02) | 4.8 (0.4) | 11.8 (0.4) | 0.25 (0.04) |
| Example 4 | 0.85 (0.04) | 1.30 (0.03) | 4.2 (0.5) | 12.5 (0.3) | 0.01 (0.01) |
| Example 5 | 0.49 (0.02) | 1.44 (0.01) | 4.8 (0.2) | 11.6 (0.3) | 0.01 (0.01) |
| Example 6 | 0.85 (0.02) | 0.75 (0.01) | 4.5 (0.5) | 11.5 (0.4) | 0.25 (0.04) |
| Example 7 | 0.85 (0.03) | 1.30 (0.02) | 4.2 (0.4) | 12.9 (0.3) | 0.01 (0.01) |
| Example 8 | 0.86 (0.02) | 1.20 (0.01) | 5.0 (0.2) | 13.2 (0.3) | 0.01 (0.01) |
| Example 9 | 0.85 (0.04) | 0.71 (0.02) | 5.3 (0.3) | 11.9 (0.4) | 0.25 (0.05) |
| Example 10 | 0.79 (0.05) | 1.10 (0.02) | 3.9 (0.4) | 13.5 (0.4) | 0.05 (0.02) |
| Example 11 | 0.85 (0.03) | 0.88 (0.03) | 3.5 (0.3) | 14.0 (0.5) | 0.12 (0.03) |
| Example 12 | 0.92 (0.05) | 0.60 (0.03) | 3.3 (0.4) | 15.2 (0.5) | 0.20 (0.03) |
| After the Pneumatic Transportation | | | | | |
| Example 1 | 0.89 (0.04) | 1.35 (0.02) | 4.5 (0.3) | 12.0 (0.3) | 0.01 (0.01) |
| Example 2 | 0.52 (0.03) | 1.44 (0.02) | 4.7 (0.3) | 11.2 (0.3) | 0.01 (0.01) |
| Example 3 | 0.72 (0.03) | 0.79 (0.03) | 4.8 (0.4) | 11.4 (0.5) | 0.26 (0.03) |
| Example 4 | 0.84 (0.04) | 1.31 (0.03) | 4.2 (0.5) | 12.3 (0.3) | 0.01 (0.01) |
| Example 5 | 0.48 (0.03) | 1.44 (0.01) | 4.6 (0.3) | 11.6 (0.4) | 0.01 (0.01) |
| Example 6 | 0.84 (0.02) | 0.76 (0.02) | 4.2 (0.4) | 11.4 (0.4) | 0.25 (0.04) |
| Example 7 | 0.84 (0.04) | 1.29 (0.02) | 4.2 (0.4) | 12.7 (0.3) | 0.01 (0.01) |
| Example 8 | 0.85 (0.03) | 1.20 (0.02) | 4.9 (0.3) | 13.0 (0.4) | 0.01 (0.01) |
| Example 9 | 0.85 (0.05) | 0.70 (0.03) | 5.2 (0.3) | 11.7 (0.5) | 0.26 (0.05) |
| Example 10 | 0.77 (0.06) | 1.10 (0.02) | 3.9 (0.4) | 13.3 (0.3) | 0.06 (0.02) |
| Example 11 | 0.87 (0.04) | 0.85 (0.04) | 3.5 (0.4) | 13.7 (0.5) | 0.12 (0.03) |
| Example 12 | 0.91 (0.06) | 0.62 (0.02) | 3.2 (0.5) | 15.0 (0.6) | 0.21 (0.04) |

*: The numeral in each parenthesis is a standard deviation (number of tests: n = 5).

TABLE 3

[Various Characteristics (B) of Examples 1 to 12]

Casting Gold Alloy for Metal-Cermaic Restorations

| | Mixing Operability (Affinity with Water) | Seizing of Investment | Surface Chapping of Casting | Formation of Casting Cavities Due To Shortage of Breathability |
|---|---|---|---|---|
| Example 1 | Good | Slightly seized | Not chapped | Not formed |
| Example 2 | Moderate | Not seized | Not chapped | Not formed |
| Example 3 | Slightly bad | Not seized | Not chapped | Not formed |
| Example 4 | Good | Not seized | Not chapped | Not formed |
| Example 5 | Good | Not seized | Not chapped | Not formed |
| Example 6 | Moderate | Not seized | Not chapped | Not formed |
| Example 7 | Good | Not seized | Not chapped | Not formed |
| Example 8 | Good | Not seized | Not chapped | Not formed |
| Example 9 | Moderate | Not seized | Not chapped | Not formed |
| Example 10 | Good | Not seized | Not chapped | Not formed |
| Example 11 | Moderate | Not seized | Not chapped | Not formed |
| Example 12 | Moderate | Not seized | Not chapped | Not formed |

Casting Palladium Alloy for Metal-Cermaic Restorations

| | Seizing of Investment | Surface Chapping of Casting | Formation of Casting Cavities Due To Shortage of Breathability |
|---|---|---|---|
| Example 1 | Seized | Slightly chapped | Not formed |
| Example 2 | Slightly seized | Slightly chapped | Not formed |
| Example 3 | Not seized | Not chapped | Not formed |
| Example 4 | Not seized | Not chapped | Not formed |
| Example 5 | Not seized | Not chapped | Not formed |
| Example 6 | Not seized | Not chapped | Not formed |
| Example 7 | Slightly seized | Not chapped | Not formed |
| Example 8 | Not seized | Not chapped | Not formed |
| Example 9 | Not seized | Not chapped | Not formed |
| Example 10 | Not seized | Not chapped | Not formed |
| Example 11 | Not seized | Not chapped | Not formed |
| Example 12 | Not seized | Not chapped | Not formed |

TABLE 4

[Compositions of Comparative Examples 1 to 10]

Composition (part by weight)

| | Binder | Refractory Material | Aggregate | Poly-tetra-fluoro ethylene Resin | Anionic Surfactant |
|---|---|---|---|---|---|
| Comparative Example 1 | α-Hemi-hydrated Gypsum 27 | Quartz 45/ Cristobalite 28 | — | — | — |
| Comparative Example 2 | α-Hemi-hydrated Gypsum 30 | Cristobalite 70 | — | 0.001 | — |
| Comparative Example 3 | α-Hemi-hydrated Gypsum | Quartz 67 | — | 0.005 | — |

TABLE 4-continued

[Compositions of Comparative Examples 1 to 10]

| | Composition (part by weight) | | | | |
|---|---|---|---|---|---|
| | Binder | Refractory Material | Aggregate | Poly-tetra-fluoro ethylene Resin | Anionic Surfactant |
| Comparative Example 4 | α-Hemi-hydrated Gypsum 33 | Quartz 45/ Cristo-balite 28 | — | 1.5 | — |
| Comparative Example 5 | α-Hemi-hydrated Gypsum 30 | Cristo-balite 70 | — | 2.0 | — |
| Comparative Example 6 | α-Hemi-hydrated Gypsum 33 | Quartz 67 | — | 1.0 | Sodium Dodecyl-benzene-sulfonate 0.0005 |
| Comparative Example 7 | α-Hemi-hydrated Gypsum 30 | Cristo-balite 70 | — | 1.5 | Sodium Myristyl-benzene-sulfonate 0.08 |
| Comparative Example 8 | α-Hemi-hydrated Gypsum 27 | Quartz 45/ Cristo-balite 28 | — | 2.0 | Sodium Dodecyl-benzene-sulfonate 0.1 |
| Comparative Example 9 | α-Hemi-hydrated Gypsum 27 | Quartz 45/ Cristo-balite 27 | Silicon Carbide 1 | 0.01 | — |
| Comparative Example 10 | α-Hemi-hydrated Gypsum 30 | Cristo-balite 20/ Zirconium Oxide 25 | Titanium Carbide 25 | 1.5 | Sodium Lauryl-sulfate 0.01/ Sodium Stearyl-sulfate 0.04 |

TABLE 5

[Various Characteristics (A) of Comparative Examples 1 to 10]

| | Setting Expansion Value (%) | Thermal Expansion Value (%) | Com-pressive Strength (MPa) | Volume of Particles Not Greater Than 1.9 μm (%) | Fitness Precision (Amount of Lifting) (mm) |
|---|---|---|---|---|---|
| Before the Pneumatic Transportation | | | | | |
| Comparative Example 1 | 0.90 (0.04) | 1.35 (0.02) | 4.4 (0.2) | 12.6 (0.3) | 0.01 (0.01) |
| Comparative Example 2 | 0.88 (0.02) | 1.45 (0.01) | 4.9 (0.2) | 11.6 (0.3) | 0.01 (0.01) |
| Comparative Example 3 | 0.72 (0.03) | 0.80 (0.02) | 5.2 (0.4) | 11.4 (0.5) | 0.24 (0.04) |
| Comparative Example 4 | 0.95 (0.10) | 1.31 (0.15) | 5.5 (0.7) | 11.0 (1.0) | 0.08 (0.08) |
| Comparative Example 5 | — | — | — | 9.8 (1.3) | — |
| Comparative Example 6 | 0.70 (0.02) | 0.78 (0.02) | 5.0 (0.4) | 11.4 (0.4) | 0.26 (0.05) |
| Comparative Example 7 | 1.00 (0.22) | 1.41 (0.10) | 2.8 (1.4) | 10.0 (1.2) | 0.08 (0.10) |
| Comparative Example 8 | 1.21 (0.43) | 1.33 (0.11) | 2.1 (1.6) | 9.6 (1.2) | 0.10 (0.10) |
| Comparative Example 9 | 0.85 (0.03) | 1.30 (0.02) | 4.2 (0.2) | 12.8 (0.4) | 0.01 (0.01) |
| Comparative Example 10 | 1.00 (0.35) | 0.42 (0.10) | 3.1 (1.5) | 10.0 (0.8) | 0.30 (0.15) |
| After the Pneumatic Transportation | | | | | |
| Comparative Example 1 | 0.85 (0.07) | 1.30 (0.06) | 4.3 (0.5) | 11.9 (0.7) | 0.04 (0.06) |
| Comparative Example 2 | 0.85 (0.06) | 1.42 (0.66) | 4.9 (0.3) | 10.9 (0.8) | 0.03 (0.05) |
| Comparative Example 3 | 0.70 (0.07) | 0.77 (0.06) | 5.0 (0.6) | 10.8 (0.7) | 0.27 (0.11) |
| Comparative Example 4 | 0.90 (0.15) | 1.30 (0.15) | 5.3 (0.8) | 11.0 (1.1) | 0.07 (0.08) |
| Comparative Example 5 | — | — | — | 9.6 (1.5) | — |
| Comparative Example 6 | 0.70 (0.03) | 0.76 (0.03) | 5.0 (0.4) | 11.2 (0.3) | 0.27 (0.05) |
| Comparative Example 7 | 0.93 (0.20) | 1.40 (0.12) | 2.6 (1.1) | 9.5 (0.8) | 0.06 (0.06) |
| Comparative Example 8 | 1.20 (0.40) | 1.34 (0.10) | 2.3 (1.3) | 9.2 (1.0) | 0.09 (0.08) |
| Comparative Example 9 | 0.85 (0.03) | 1.31 (0.03) | 4.1 (0.2) | 12.5 (0.3) | 0.01 (0.01) |
| Comparative Example 10 | 0.98 (0.34) | 0.40 (0.11) | 3.0 (1.3) | 9.9 (1.0) | 0.35 (0.21) |

*: The numeral in each parenthesis is a standard deviation (number of tests: n = 5).

TABLE 6

[Various Characteristics (B) of Comparative Examples 1 to 10]

| | Casting Gold Alloy for Metal-Cermaic Restorations | | | |
|---|---|---|---|---|
| | Mixing Operability (Affinity with Water) | Seizing of Investment | Surface Chapping of Casting | Formation of Casting Cavities Due To Shortage of Breathability |
| Comparative Example 1 | Moderate | Seized | Chapped | Impossible for evaluation due to surface chapping |
| Comparative Example 2 | Moderate | Seized | Chapped | Impossible for evaluation due to surface chapping |
| Comparative Example 3 | Good | Seized | Chapped | Impossible for evaluation due to surface chapping |
| Comparative Example 4 | Bad (possible for mixing) | Not seized | Not chapped | Formed in part of sprue |
| Comparative Example 5 | Impossible for mixing | — | — | — |
| Comparative Example 6 | Slightly bad | Not seized | Not chapped | Not formed |
| Comparative Example 7 | Moderate (bubbling) | Not seized | Not chapped/ Flash | Formed in part of |

TABLE 6-continued

[Various Characteristics (B) of Comparative Examples 1 to 10]

| | | | formed | sprue |
|---|---|---|---|---|
| Comparative Example 8 | Moderate (bubbling) | Not seized | Not chapped/ Flash formed | Formed in part of sprue |
| Comparative Example 9 | Good | Slightly seized | Not chapped | Not formed |
| Comparative Example 10 | Moderate | Not seized | Not chapped | Not formed |

Casting Palladium Alloy for Metal-Cermaic Restorations

| | Seizing of Investment | Surface Chapping of Casting | Formation of Casting Cavities Due To Shortage of Breathability |
|---|---|---|---|
| Comparative Example 1 | Vigorously seized | Chapped | Impossible for evaluation due to surface chapping |
| Comparative Example 2 | Vigorously seized | Chapped | Impossible for evaluation due to surface chapping |
| Comparative Example 3 | Vigorousiy seized | Chapped | Impossible for evaluation due to surface chapping |
| Comparative Example 4 | Not seized | Not chapped | Formed in part of sprue |
| Comparative Example 5 | — | — | — |
| Comparative Example 6 | Not seized | Not chapped | Not formed |
| Comparative Example 7 | Slightly seized | Not chapped/ Flash formed | Formed in part of sprue |
| Comparative Example 8 | Not seized | Not chapped/ Flash formed | Formed in part of sprue |
| Comparative Example 9 | Seized | Slightly chapped | Not formed |
| Comparative Example 10 | Not seized | Not chapped | Not formed |

The trapping effect of fine particles and the improving effect in heat resistance due to the mixing of the poly-tetrafluoroethylene resin can be confirmed by the comparison of the compositions and characteristic values as shown in Tables 1 to 6.

As is clear from the Tables, in the respective Examples, the poly-tetrafluoroethylene resin is mixed in an amount of from 0.01 to 1.0% by weight, the poly-tetrafluoroethylene resin exhibited an effect for trapping the particles of the refractory material, the binder, and the like, there was no substantial difference in the physical characteristics between before and after the pneumatic transportation, and no lowering in the casting precision was confirmed.

Also, in the respective Examples, it was possible to undergo the casting with a dental casting alloy for metal-ceramic restorations even as to any gypsum bonded investments. Even in the case of Example 1 which may be considered to have the lowest heat resistance, as is clear from Table 3, in casting with the G-Cera Bond Type III Palladium Alloy having a high liquidus point, while the seizing phenomenon of the investment was found, such was still in a range possible for the clinical applications.

On the other hand, in Comparative Example 1 in which no poly-tetrafluoroethylene resin is added and Comparative Examples 2 and 3 in which the mixing amount of the poly-tetrafluoroethylene resin is less than the lower limit of the range according to the present invention, the fine particles in the gypsum bonded investment were lost during the pneumatic transportation. As a result, the lowering in the fitness precision and the increase in the scattering were found after the pneumatic transportation, whereby the effect to be brought by the mixing of the poly-tetrafluoroethylene resin was not exhibited.

Specifically, after the pneumatic transportation, not only the setting expansion value and the thermal expansion value, both of which are the characteristics influencing the dimensional precision of the casting, were lowered as compared with those before the pneumatic transportation, but also the fitness precision of the casting was lowered. Also, the value of the standard deviation increased. Thus, in case that the casting is carried out by using the gypsum bonded investments of these Comparative Examples, it can be confirmed that the casting precision becomes worse and that the scattering of the casting precision is likely formed.

Also, in the results obtained after observing the casting surface, the casting defects were remarkably formed, and it was impossible to apply the castings to the clinical use. In comparison between Examples 1 to 3 and Comparative Examples 1 to 3, while the respective compositions are substantially identical, only the mixing amount of the poly-tetrafluoroethylene resin is different. From the investigation of these results, it was confirmed that the mixing of the gypsum bonded investment with the poly-tetrafluoroethylene resin remarkably improved the heat resistance of the casting mold.

Comparative Examples 4, 5, 7, 8 and 10 are an example in which the mixing amount of the poly-tetrafluoroethylene resin exceeds the upper limit of the range according to the present invention. By mixing an excess of the tetrafluoroethylene resin, in the step of discharging the gypsum bonded investment from the mill, a phenomenon in which the powders of the gypsum bonded investment cohered to each other occurred, the amount to be discharged from the exhaust port was reduced, the revolution of the mill for the discharge resulted in grinding of the remaining investment to cause excessive grinding, the differences in the setting expansion, the thermal expansion, and the like became large, and the scattering was generated in the characteristic values of the investment before the pneumatic transportation.

Also, the poly-tetrafluoroethylene resin is a substance having particularly strong water repellency. In Comparative Examples 4 and 5 in which the mixing amount of the poly-tetrafluoroethylene resin is from 1.5 to 2.0 parts by weight, the amount of which exceeds the upper limit of the range according to the present invention, and no anionic surfactant is compounded, the mixing properties became extremely worse so that it was impossible to undergo the mixing by the usual mixing method of a gypsum bonded investment in the dentistry. In particular, in Comparative Example 5, not only even when the mixing machine was used, the mixing could not be effected, but also the characteristics could not be evaluated. In Comparative Example 4, the mixing could be barely effected by means of mechanical mixing, and the evaluations in the seizing of investment and in the surface chapping of casting were good due to the effect of the poly-tetrafluoroethylene resin. However, by the mixing of the poly-tetrafluoroethylene resin in excess, calcium fluoride was excessively formed in the casting mold. As a result, the breathability of the casting mold was extremely lowered, leading to the generation of casting defects such as back pressure porosity, formation of hot spots, etc. in part of the sprue.

Example 1 is a case that only the poly-tetrafluoroethylene resin having strong water repellency is mixed. In this case, if the mixing amount of the poly-tetrafluoroethylene resin is low as about 0.01 part by weight, even when no anionic surfactant was compounded in the gypsum bonded investment, the characteristic of the affinity with water was "good". This evaluation was made through the comparison with the currently used gypsum bonded investment products, the evaluation "good" means that the affinity with water is higher than that of the currently used gypsum investment products, and the evaluation "moderate" means that it is equal to that of the currently used ones. If the mixing amount of the poly-tetrafluoroethylene resin is low as about 0.01 part by weight, it was found that contrary to our expectations by the mixing of a strong water repellent, the mixing properties were improved as compared with those of the currently used products. It may be considered that this is because by mixing the poly-tetrafluoroethylene resin having strong water repellency, though the affinity of the investment powder became worse microscopically, since no curdling occurred because of good hydrophilicity between the investment powder and water, the mixing properties were improved, and hence, the evaluation with respect to the affinity with water became good macroscopically (organoleptic examination). In Example 2 in which the mixing amount of the poly-tetrafluoroethylene resin increases to 0.1 part by weight, the affinity with water was lowered to the evaluation "moderate", which was, however, still substantially equal to that of the currently used gypsum bonded investments. In addition, in Example 3 in which the mixing amount of the poly-tetrafluoroethylene resin is high, the evaluation was lowered to "slightly bad". Specifically, the evaluation "slightly bad" means that though it is possible to undergo the mixing and prepare a casting mold in the practical use, the affinity with water is slightly worse than that of the currently used products, and the mixing properties are a few inferior.

As described previously, by mixing the poly-tetrafluoroethylene resin having strong water repellency in the dental gypsum bonded investment, the mixing properties are lowered. In Examples 4 to 6 and 10 to 12, in order to improve this characteristic, the anionic surfactant is mixed. By mixing the anionic surfactant, improvements in the mixing properties were found.

Specifically, in the comparison between Example 3 and Example 6, the difference in the compounding is whether the anionic surfactant is mixed or not. In Example 3, the evaluation in the mixing operability is "slightly bad", while in Example 6, it is "moderate". Thus, by mixing the anionic surfactant, the mixing operability is improved.

On the other hand, in Comparative Example 6 in which the mixing amount of the poly-tetrafluoroethylene resin is 1.0 part by weight as the upper limit, for the purpose of improving the affinity with water, the anionic surfactant is mixed in an amount of 0.0005 part by weight. In this Comparative Example, since the mixing amount of the anionic surfactant is too low, no improving effect was found in the comparison with Example 3 in which no anionic surfactant is mixed.

As problems in the case that the anionic surfactant is mixed in the gypsum bonded investment, there are the lowering in the compressive strength and the prolongation in the setting time. By these problems, a casting defect called "casting flash", which is caused by the shortage in the strength of the casting mold, possibly occurs. It has been hitherto proven through studies that as factors for determining the compressive strength of the casting mold, the compounding amount and properties of α-hemihydrate gypsum as the binder occupy a major part and that the refractory material and the aggregate as other constituent components of the gypsum bonded investment do not give great influences. For this reason, as the cause of the lowering in the compressive strength, it may be considered that the anionic surfactant mixed inhibits the growth of the crystal of α-hemihydrate gypsum as the binder of the gypsum bonded investment into a needle-like state and makes it crystallize into a tabular state, leading to the lowering in the compressive strength of the casting mold. It is already proven through the studies as well as the quality examinations of products which have hitherto been carried out that the lowest compressive strength for forming no casting flash is 3 MPa as a border line.

In the comparison between Examples 1 to 3 and Examples 4 to 6, when the mixing amount of the anionic surfactant is up to about 0.01 part by weight, the lowering in the compressive strength was little, and no formation of the casting flash was found. However, in the samples in which the mixing amount of the anionic surfactant is high, the lowering in the compressive strength was found. Specifically, in Examples 1 and 4 in which the compounding amount of α-hemihydrate gypsum is equal to, but the mixing amount of the anionic surfactant is different from each other, the compressive strength was lowered from 4.4 MPa to 4.2 MPa. Similarly, in Examples 2 and 5, the compressive strength was lowered from 5.0 MPa to 4.8 MPa, and in Examples 3 and 6, the compressive strength was lowered from 4.8 PMa to 4.5 PMa. In Examples 10, 11 and 12 in which the mixing amount of the anionic surfactant is from 0.02 to 0.04 part by weight, while the compressive strength was lowered, it exceeded 3 MPa as the border line at which no casting flash was formed, and in actual casting experiments, the formation of casting flash was not found.

However, in the samples in which the mixing amount of the anionic surfactant is high, the lowering in the compressive strength was remarkable, and the formation of casting defects was found. In Comparative Examples 7 and 8, the mixing amount of the poly-tetrafluoroethylene resin is high as from 1.5 to 2.0 parts by weight, and in order to improve the mixing properties, the aninoic surfactant is mixed in an amount as high as from 0.08 to 0.1 part by weight. In Comparative Example 7 and Example 2, nevertheless the major components are the same as each other, since in Comparative Example 7, the anionic surfactant was mixed in a higher amount, the compressive strength was low as 2.8 PMa, the value of which was lowered by 40% as compared with that in Example 2, and was less than 3 MPa as the border line, and hence, in the casting tests, the formation of casting flash was found. Similarly, in the comparison between Comparative Example 8 and Example 1, in Comparative Example 8 in which the mixing amount of the anionic surfactant is high as 0.1 part by weight, the compressive strength was 2.1 MPa, the value of which was lowered by about 50% as compared with that in Example 1, and the formation of casting flash was found.

The casting mold prepared by using the gypsum bonded investment composition having a poly-tetrafluoroethylene resin mixed therewith according to the present invention is improved in the heat resistance and has made it possible to undergo casting with casting alloys for metal-ceramic restrations, which has hitherto been considered impossible.

However, in case that the mixing amount of the poly-tetrafluoroethylene resin is low, there may be cases that a phenomenon in which the investment components are seized on the casting occurs, or the surface chapping occurs. Even in such cases, while not only the degree of the occurrence of such a phenomenon is light, but also it is possible to apply the casting to the clinical use, since the sandblast processing works are necessary for the removal of the seized investment, and the polishing works are necessary for the elimination of the surface chapping, it is expected that the dental technology operations become complicated. In order to avoid these phenomena, it is effective to compound a substance which has a poor wettability with the molten metal to be casted and that is poorly reactive therewith into the gypsum bonded investment. In the present invention, experiments were carried out such that as such a substance, a part of the refractory material was replaced by and mixed with an aggregate comprising metallic oxides, metallic carbides, or metallic nitrides, and the results as shown in the Examples and Comparative Examples were obtained.

The difference between Examples 1 and 7 resides only in the matter that 1 part by weight of each of quartz and cristobalite is substituted with silicon carbide and boron nitride, respectively. With respect to the evaluation results of the casting defects in Example 1, since the mixing amount of the poly-tetrafluoroethylene resin is 0.01 part by weight as the lower limit, the phenomenon of seizing of the gypsum bonded investment and the surface chapping were observed. On the other hand, in Example 7 in which the aggregate is compounded in an amount of 2 parts by weight in total, the improvement in the phenomenon of seizing of the gypsum bonded investment was found, and the surface chapping could be completely prevented. Similarly, in Example 8 in which 2 parts by weight of each of quartz and cristobalite in the composition of Example 1 is substituted with titanium oxide and titanium carbide, respectively, the casting quite free from the generation of the seizing of the gypsum bonded investment and of the surface chapping could be obtained.

On the other hand, in Comparative Example 9 in which 1 part by weight of cristobalite in the composition of Example 1 is substituted with silicon carbide to thereby intend to prevent the generation of the casting defects, the effect against the casting defects was not distinct as compared with that of Example 1. It has been understood from these results that in case that metallic oxides, metallic carbides, or metallic nitrides are compounded as the aggregate in the gypsum bonded investment to inhibit the casting defects such as the seizing of the investment, the compounding amount of the aggregate is desirably 2 parts by weight or more.

The improvements in the seizing of the investment on the casting and in the surface chapping by the addition of metallic oxides, metallic carbides, or metallic nitrides as the aggregate are confirmed in Examples 7 to 12. In particular, in Examples 11 and 12, since the mixing amount of the poly-tetrafluoroethylene resin is 1.0 part by weight as the upper limit of the range according to the present invention, and the compounding amount of the aggregate is high, the heat resistance was improved to such an extent that no difference is found as compared with the phosphate bonded investment.

As necessary conditions for the dental investment, various conditions are enumerated. Among them, it is the most important condition to have the expansion so as to compensate the shrinkage at the time of casting of a casting metal. In the current dental casting system, it is a distinct fact that this condition is very important. Judging from various experiments and search of literatures, the expansion amount necessary for compensating the casting shrinkage of casting alloys for metal-ceramic restorations is at least 1.5% of the sum of the setting expansion value and the thermal expansion value.

It has been confirmed that to compound metallic oxides, metallic carbides, or metallic nitrides as the aggregate is useful for preventing the casting defects. However, since the reduction of the amount of $\alpha$-hemihydrate gypsum for the purpose of ensuring the compounding amount of the aggregate leads to a remarkable reduction of the compressive strength of the casting mold and causes casting defects such as the formation of casting flash, and hence, there may be a fear that it is impossible to put it into the practical use, it is unavoidable to substitute a part of the refractory material such as quartz and cristobalite with the aggregate. However, metallic oxides, metallic carbides, or metallic nitrides as the aggregate do not have such a nature that the crystal form changes (transforms) at a specific temperature, as in cristobalite or quartz as the refractory material, and can not be expected to cause the thermal expansion. For these reasons, to compound metallic oxides, metallic carbides, or metallic nitrides in the gypsum bonded investment lowers the thermal expansion value as far as possible, leading to the occurrence of a phenomenon in which no expansion necessary for compensating the casting shrinkage is obtained.

In Example 12 in which the compounding amount of the aggregate is 40 parts by weight in total, the sum of the setting expansion value and the thermal expansion value barely exceeded 1.5%. On the other hand, in Comparative Example 10, since the compounding amount of the aggregate is 50 parts by weight in total, and the thermal expansion is lowered, the whole expansion value was below 1.5% as the border line, and hence, it was impossible to compensate the casting shrinkage. It has been understood from these results that in case that it is intended to improve the seizing of the investment and the surface chapping by compounding metallic oxides, metallic carbides, or metallic nitrides as the aggregate, the compounding amount of the aggregate is desirably not more than 40 parts by weight.

As described previously in detail, since the dental gypsum bonded investment composition according to the present invention, in which a mixture comprising $\alpha$-hemihydrate gypsum as a binder and quartz and/or cristobalite as a refractory material is mixed with a poly-tetrafluoroethylene resin, and the poly-tetrafluoroethylene resin is rendered in a fibrous state in a grinding step, whereby the fine particles in the investment are trapped to enable to prevent losses of the fine particles in a pneumatic transportation step, dental gypsum bonded investments having stable characteristic values such as setting expansion values and thermal expansion values can be obtained, and hence, it is now possible to prepare dental metal restorations having a high dimensional precision.

Also, by mixing the poly-tetrafluoroethylene resin in the dental gypsum bonded investment composition, the tetrafluoroethylene resin changes into a hydrogen fluoride gas in a heating step of a casting mold in a furnace after the investment, which is then reacted with anhydrous gypsum into which $\alpha$-hemihydrate gypsum as the binder has changed upon heating in the casting mold, to form calcium fluoride with high heat resistance, whereby the heat resistance of the casting mold itself is improved. As a result, it is now possible to undergo casting of casting alloys for metal-ceramic restorations by using the gypsum bonded investment, the matter of which has hitherto been considered to be impossible by the conventional technologies.

Also, as an incidental effect, by the trapping effect of the fine particles by mixing the poly-tetrafluoroethylene resin and rendering it in a fibrous state in the grinding step, an effect for preventing the flying of the fine particles in the gypsum bonded investment at the time of mixing operation of the investment in the preparation of casting molds is obtained.

Also, against the problem that the mixing operability becomes worse by mixing the poly-tetrafluoroethylene resin having high water repellency, it is now possible to overcome it by mixing one or more anionic surfactants selected from the group consisting of alkylbenzenesulfonates and alkylsulfates.

In addition, for the purposes of preventing the seizing of the investment on the casting as well as of preventing the surface chapping, it is now confirmed to be effective to mix metallic oxides, metallic carbides, or metallic nitrides as the aggregate.

In the light of the above, the dental gypsum bonded investment composition having the above described various effects according to the present invention is very valuable for contribution towards the dental field.

While the invention has been described in detail and with reference to specific embodiments thereof, it will be apparent to one skilled in the art that various changes and modifications can be made therein without departing from the spirit and scope thereof.

What is claimed is:

1. A dental gypsum bonded investment composition comprising 100 parts by weight of (A) a mixture comprising (a) α-hemihydrate gypsum as a binder and (b) quartz and/or cristobalite as a refractory material, and (B) from 0.01 to 1.0 part by weight of a poly-tetrafluoroethylene resin.

2. A dental gypsum bonded investment composition comprising 100 parts by weight of (A) a mixture comprising (a) α-hemihydrate gypsum as a binder and (b) quartz and/or cristobalite as a refractory material, (B) from 0.01 to 1.0 part by weight of a poly-tetrafluoroethylene resin and (C) from 0.001 to 0.05 part by weight of one or more anionic surfactants selected from the group consisting of alkylbenzenesulfonates and alkylsulfates.

3. A dental gypsum bonded investment composition comprising 100 parts by weight of (A) a mixture comprising (a) α-hemihydrate gypsum as a binder and (b) quartz and/or cristobalite as a refractory material, and (c) one or more aggregates selected from the group consisting of metallic oxides, metallic carbides, and metallic nitrides, and (B) from 0.01 to 1.0 part by weight of a poly-tetrafluoroethylene resin.

4. A dental gypsum bonded investment composition comprising 100 parts by weight of (A) a mixture comprising (a) α-hemihydrate gypsum as a binder and (b) quartz and/or cristobalite as a refractory material, and (c) one or more aggregates selected from the group consisting of metallic oxides, metallic carbides and metallic nitrides, (B) from 0.01 to 1.0 part by weight of a poly-tetrafluoroethylene resin and (C) from 0.001 to 0.05 part by weight of one or more anionic surfactants selected from the group consisting of alkylbenzenesulfonates and alkylsulfates.

5. The composition of claim 1, wherein binder (a) is present in an amount of from 20 to 40 parts by weight and refractory material (b) is present in an amount of from 60 to 80 parts by weight, based on 100 parts by weight of (A).

6. The composition of claim 2, wherein binder (a) is present in an amount of from 20 to 40 parts by weight and refractory material (b) is present in an amount of from 60 to 80 parts by weight, based on 100 parts by weight of (A).

7. The composition of claim 3, wherein binder (a) is present in an amount of from 20 to 40 parts by weight, refractory material (b) is present in an mount of from 20 to 78 parts by weight, and aggregate (c) is present in an amount of from 2 to 40 parts by weight, based on 100 parts by weight of (A).

8. The composition of claim 4, wherein binder (a) is present in an amount of from 20 to 40 parts by weight, refractory material (b) is present in an amount of from 20 to 78 parts by weight, and aggregate (c) is present in an amount of from 2 to 40 parts by weight, based on 100 parts by weight of (A).

* * * * *